(12) United States Patent
Ryan et al.

(10) Patent No.: US 12,246,170 B2
(45) Date of Patent: Mar. 11, 2025

(54) HINGED NEEDLE SHIELD AND NEEDLE ASSEMBLIES

(71) Applicant: Becton, Dickinson and Company, Franklin Lakes, NJ (US)

(72) Inventors: Kevin M. Ryan, Whitehouse Station, NJ (US); Angela Huenerfauth, Morristown, NJ (US); Thomas Anthony Pick, Columbus, NE (US); Ramon Arazo, Fraga Huesca (ES); Miguel Luis Nogues Rubio, Torrente de Cinca (ES)

(73) Assignee: Becton, Dickinson and Company, Franklin Lakes, NJ (US)

( * ) Notice: Subject to any disclaimer, the term of this patent is extended or adjusted under 35 U.S.C. 154(b) by 853 days.

(21) Appl. No.: 17/017,263

(22) Filed: Sep. 10, 2020

(65) Prior Publication Data
US 2021/0077744 A1 Mar. 18, 2021

Related U.S. Application Data

(60) Provisional application No. 62/901,603, filed on Sep. 17, 2019, provisional application No. 62/900,147, filed on Sep. 13, 2019.

(51) Int. Cl.
*A61M 5/32* (2006.01)
*A61M 5/34* (2006.01)

(52) U.S. Cl.
CPC ........ *A61M 5/3216* (2013.01); *A61M 5/3202* (2013.01); *A61M 5/3204* (2013.01); *A61M 5/34* (2013.01); *A61M 2205/582* (2013.01)

(58) Field of Classification Search
CPC .... A61M 5/3204; A61M 5/34; A61M 5/3216; A61M 2205/582; A61M 2205/0216; A61M 2205/273
See application file for complete search history.

(56) References Cited

U.S. PATENT DOCUMENTS 5,242,417 A 9/1993 Paudler
5,681,295 A 10/1997 Gyure et al.
(Continued)

FOREIGN PATENT DOCUMENTS

EP 0885621 B1 12/2002

OTHER PUBLICATIONS

PCT International Search Report and Written Opinion in PCT/US2020/050279 dated Feb. 25, 2021, 19 pages.

*Primary Examiner* — Tasnim Mehjabin Ahmed
(74) *Attorney, Agent, or Firm* — Servilla Whitney LLC (57) ABSTRACT

A needle shield assembly comprises an elongate needle shield comprising a shield portion, a hub connection portion and a bridge portion including a living hinge having a thickness, the bridge portion joining the hub connection portion and the shield portion, the hub connection portion comprising a receiving ring having a diameter sized to frictionally receive the hub outer surface when the needle assembly is inserted through the receiving ring and a flange extending from the receiving ring defining a top planar surface and a bottom surface. The thickness of the flange divided by the thickness of the living hinge defines a ratio of from 1.1 to 6. The shield portion is configured to pivot from an open position in which the needle cannula is exposed, to a closed needle protecting position in which the distal end of the needle cannula is within the longitudinal opening of the shield.

26 Claims, 11 Drawing Sheets

(56) References Cited

U.S. PATENT DOCUMENTS

| | | | |
|---|---|---|---|
| 8,251,961 B2 | 8/2012 | Hauri et al. | |
| 2002/0156427 A1* | 10/2002 | Suzuki | A61M 5/3216 604/198 |
| 2003/0212369 A1 | 11/2003 | Kobayashi | |
| 2005/0065481 A1* | 3/2005 | Hauri | A61M 5/3202 604/263 |
| 2008/0208138 A1* | 8/2008 | Lim | A61M 5/3216 604/192 |

\* cited by examiner

HINGED NEEDLE SHIELD AND NEEDLE ASSEMBLIES

CROSS-REFERENCE TO RELATED APPLICATIONS

This application claims priority to U.S. Provisional Application Nos. 62/900,147, filed on Sep. 13, 2019 and 62/901,603 filed on Sep. 17, 2019, the entire disclosures of which are hereby incorporated by reference herein.

FIELD OF THE DISCLOSURE

The present disclosure generally relates to needle assemblies having safety features and more specifically to a needle assembly having a hinged needle shield assembly for use with a syringe.

BACKGROUND OF THE DISCLOSURE

Accidental needle sticks with new unused needle can cause injury and render the needle unfit for further use. Accidental needle sticks with a used needle can transmit disease. As a result, most prior art needle assemblies have a needle shield. Some prior art needle shields define a rigid sleeve that can be manually telescoped over a needle cannula. This procedure requires a healthcare worker to hold the syringe barrel in one hand and the shield in the other. Some medical procedures require the application of pressure to the penetration site after the needle has been removed. Thus, healthcare workers are often unable to use both hands for shielding the needle cannula. In these situations, workers merely deposit the used medical implement on a nearby surface with the intention of shielding at a more convenient time. However, until the needle is shielded or properly disposed of, it presents a potential danger to other people.

A needle shield which is hinged near the base of the needle has the advantage of allowing one-handed needle reshielding, providing the opportunity for reshielding by a medical practitioner, under most circumstances, immediately after use.

Various means have been provided for locking a hinged needle shield in the closed, needle protecting, position. Deflectable members have been provided in the needle shield for engaging the needle upon shielding and preventing subsequent unshielding of the needle. Such members trap the needle within the needle shield. Locking has also been accomplished by locking engagement of the needle shield with structure near the base of the needle.

There is still a need for an improved hinged needle shield that is cost effective and easy to manufacture.

SUMMARY OF THE DISCLOSURE

A first embodiment pertains to a needle shield assembly for use with a needle assembly including a needle cannula having a proximal end, a distal end and a lumen therethrough, and a hub having an outer surface, an open proximal end including a cavity therein and a distal end attached to the proximal end of the needle cannula so that the lumen is in fluid communication with the cavity comprising an elongate needle shield comprising a shield portion, a hub connection portion and a bridge portion including a living hinge having a thickness, the bridge portion joining the hub connection portion and the shield portion, the hub connection portion comprising a receiving ring having a diameter sized to frictionally receive the hub outer surface when the needle assembly is inserted through the receiving ring and a flange extending from the receiving ring defining a top planar surface and a bottom surface, the flange having a thickness, the thickness of the flange divided by the thickness of the living hinge defining a ratio of from 1.1 to 6, the shield portion having two side walls defining a longitudinal opening and a back wall between the side walls defining a recess having an interior surface, the shield portion configured to pivot from an open position in which the needle cannula is exposed, to a closed needle protecting position in which the distal end of the needle cannula is within the longitudinal opening of the shield.

A second embodiment pertains to a needle shield and needle assembly comprising a needle assembly including a needle cannula having a proximal end, a distal end and a lumen therethrough, and a hub having an outer surface, an open proximal end including a cavity therein and a distal end attached to the proximal end of the needle cannula so that the lumen is in fluid communication with the cavity; and an elongate needle shield comprising a shield portion, a hub connection portion and a bridge portion including a living hinge having a thickness, the bridge portion joining the hub connection portion and the shield portion, the hub connection portion comprising a receiving ring having a diameter sized to frictionally receive the hub outer surface when the needle assembly is inserted through the receiving ring and a flange extending from the receiving ring defining a top planar surface and a bottom surface, the flange having a thickness, the thickness of the flange divided by the thickness of the living hinge defining a ratio of from 1.1 to 6, the shield portion having two side walls defining a longitudinal opening and a back wall between the side walls defining a recess having an interior surface, the shield portion configured to pivot from an open position in which the needle cannula is exposed, to a closed needle-protecting position in which the distal end of the needle cannula is within the longitudinal opening of the shield.

DETAILED DESCRIPTION

While this disclosure is satisfied by embodiments in many different forms, there are shown in the drawings and will herein be described in specific embodiments of the disclosure with the understanding that the present disclosure is to be considered exemplary of the principles and are not intended to limit the disclosure to the embodiments illustrated. The scope of the disclosure will be measured by the appended claims and their equivalents.

Referring to FIGS. 1-9, a needle shield assembly 100 for use with a needle assembly 200 including a needle cannula 202 having a proximal end 203, a distal end 205 and a lumen 206 therethrough. The needle assembly 200 further comprises a hub 208 having an outer surface 209, an open proximal end 210 including a cavity 212 therein and a distal end 214 attached to the proximal end 203 of the needle cannula 202 so that the lumen 206 is in fluid communication with the cavity 212.

The needle shield assembly 100 comprises shield portion 102, a hub connection portion 104 and a bridge portion 106 including a living hinge 108 having a thickness TH, the bridge portion 106 joining the hub connection portion 104 and the shield portion 102. The hub connection portion 104 comprises a receiving ring 112 having a diameter D sized to frictionally receive the hub outer surface 209 when the needle assembly 200 is inserted through the receiving ring 112 and a flange 114 extending from the receiving ring 112 defining a top planar surface 116 and a bottom surface 118. The distance between the top planar surface and the bottom surface 118 defines a flange thickness TF. In one or more embodiments, the thickness of the flange TF divided by the thickness of the living hinge TH defines a ratio of from 1.1 to 6. In one or more embodiments, the thickness of the flange TF divided by the thickness of the living hinge TH defines a ratio of from 1.2 to 6, 1.3 to 6, 1.4 to 6, 1.5 to 6, 1.6 to 6, 1.7 to 6, 1.8 to 6, 1.9 to 6, 2 to 6, 2.1 to 6, 2.2 to 6, 2.3 to 6, 2.4 to 6, 2.5 to 6, 2.6 to 6, 2.7 to 6, 2.8 to 6, 2.9 to 6, 3 to 6, 1.1 to 5, 1.2 to 5, 1.3 to 5, 1.4 to 5, 1.5 to 5, 1.6 to 5, 1.7 to 5, 1.8 to 5, 1.9 to 5, 2 to 5, 2.1 to 5, 2.2 to 5, 2.3 to 5, 2.4 to 5, 2.5 to 5, 2.6 to 5, 2.7 to 5, 2.8 to 5, 2.9 to 5, 3 to 5, 1.1 to 4, 1.2 to 4, 1.3 to 4, 1.4 to 4, 1.5 to 4, 1.6 to 4, 1.7 to 4, 1.8 to 4, 1.9 to 4, 2 to 4, 2.1 to 4, 2.2 to 4, 2.3 to 4, 2.4 to 4, 2.5 to 4, 2.6 to 4, 2.7 to 4, 2.8 to 4, 2.9 to 4, 3 to 4.

If the thickness of the living hinge TH is too great, the living hinge will not be flexible enough, and the shield will not be easily closed over the needle cannula. On the other hand, if the thickness of the living hinge TH is too small, the living hinge will be prone to breaking. In one or more embodiments, the ratio defined by the thickness of the flange TF divided by the thickness of the living hinge TH is within the above provided ranges. If the ratio defined by the thickness of the flange TF divided by the thickness of the living hinge TH is outside the defined ranges, the needle shield will be difficult to manufacture by injection molding because when the ratio is too low, insufficient material will flow to form the bridge portion 106 and the hub connection portion 104 of the needle shield assembly 100. In one or more embodiments, in addition to being within the ratios provided above, the living hinge 108 has a thickness TH in a range of from 0.1 mm to 0.3 mm, for example 0.1 mm, 0.15 mm, 0.2 mm, 0.25 mm or 0.3 mm) and the flange TF 114 has a thickness in a range of from 0.4 mm to 0.8 mm (for example 0.4 mm, 0.45 mm, 0.5 mm, 0.55 mm, 0.60 mm, 0.65 mm, 0.70 mm, 0.75 mm or 0.80 mm). In addition, if the thickness of the flange 114 is too small, the flange 114 will have insufficient structural integrity to withstand insertion of the hub 208 through the receiving ring 112. However, if the thickness of the flange TF is outside the upper end of the ranges provided and not within the ratios provided above, it will be difficult to form the part by injection molding.

Figure 8:
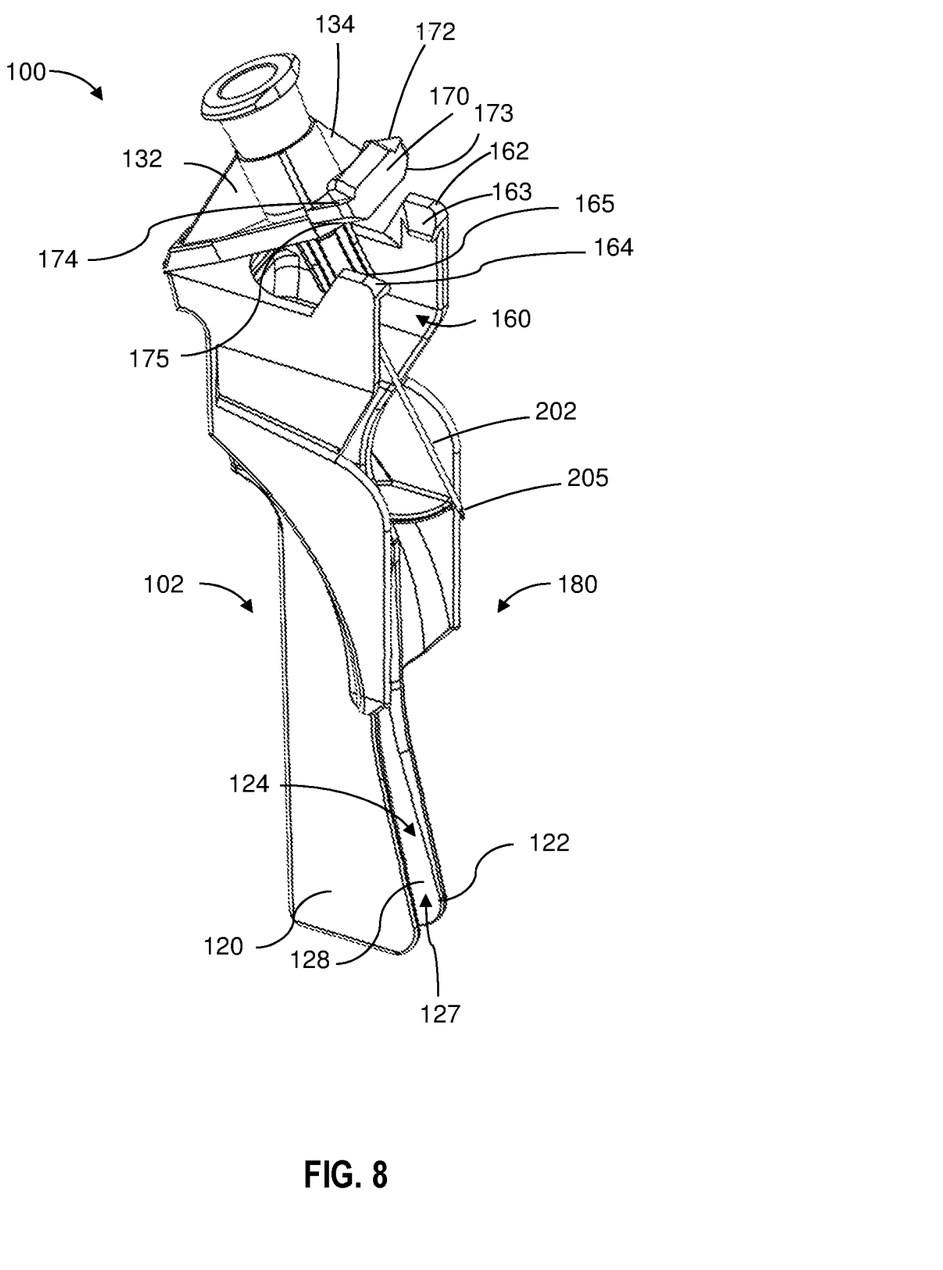
FIG. 8 is a perspective view of the needle assembly shown in FIG. 1 with the shield in a partially folded position.

The shield portion 102 has two side walls, a first side wall 120 and a second sidewall 122, defining a longitudinal opening 124 and a back wall 126 between the side walls 120, 122 defining a recess 127 having an interior surface 128. The shield portion 102 is configured to pivot from an open position in which the needle cannula is exposed (see e.g., FIG. 1 and FIG. 7) towards a closed protected position 180 (see FIG. 8) in which the distal end 205 of the needle cannula 202 is protected within the longitudinal opening 124 of the shield as shown in FIG. 8. It will be appreciated for the purposes of illustration that in FIG. 8, the protected position 180 is not in the fully closed position, but in a nearly closed position.

In one or more embodiments, the receiving ring 112 further comprises a cylindrical wall extension 130 which extends below the bottom surface 118 of the flange 114 to provide a cylindrical receiving structure 130 for the hub. In one or more embodiments, the needle shield assembly comprises a plurality of ribs 132, 134 extending from the bottom surface 118 and radially extending from the cylindrical wall extension 130. In some embodiments, the plurality of ribs comprises from 3 to 8 ribs. In some embodiments, the plurality of ribs 132, 134 comprises from 3 to 5 ribs, for example 4 ribs. The ribs 132, 134 provide additional structural integrity to the flange 114, which also allows the thickness of the flange TF to be reduced.

In some embodiments, the bridge portion 106 comprising a first span 142 spaced apart from a second span 144 to provide a gap 146 between the first span 142 and the second span 144, and the living hinge 108 having a first portion 108a joining the first span 142 to the shield portion 102 and a second portion 108b joining the second span 144 to the shield portion 102. In one or more embodiments, the first span 142 and the second span 144 each comprise a width WS, and the gap 146 comprises a width WG such that the width of the gap WG is greater than the width WS of the first span and the width WS of the second span.

Figure 1:
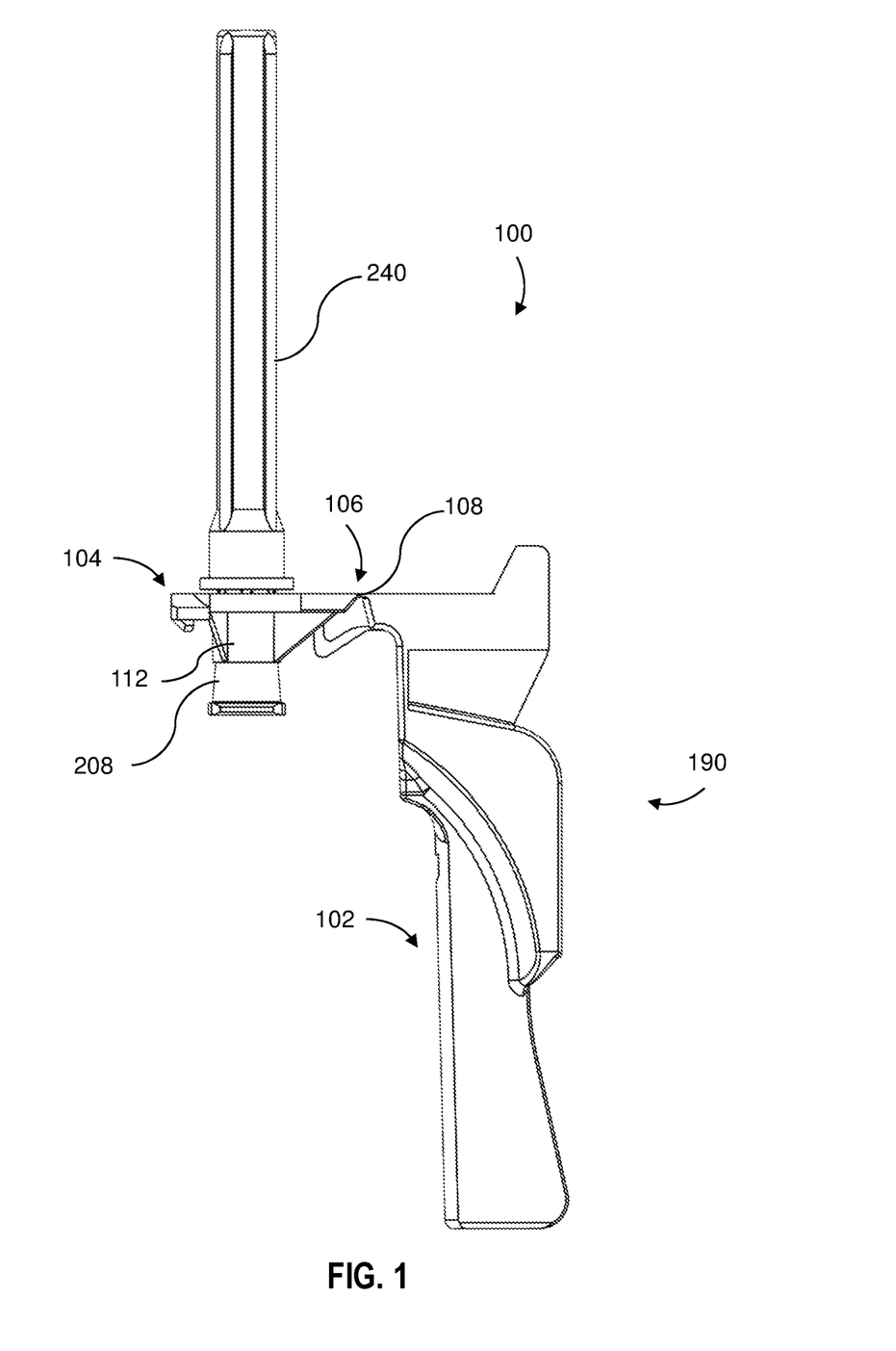
FIG. 1 is side elevation view of a needle assembly according to an embodiment of the present disclosure.
Figure 2:
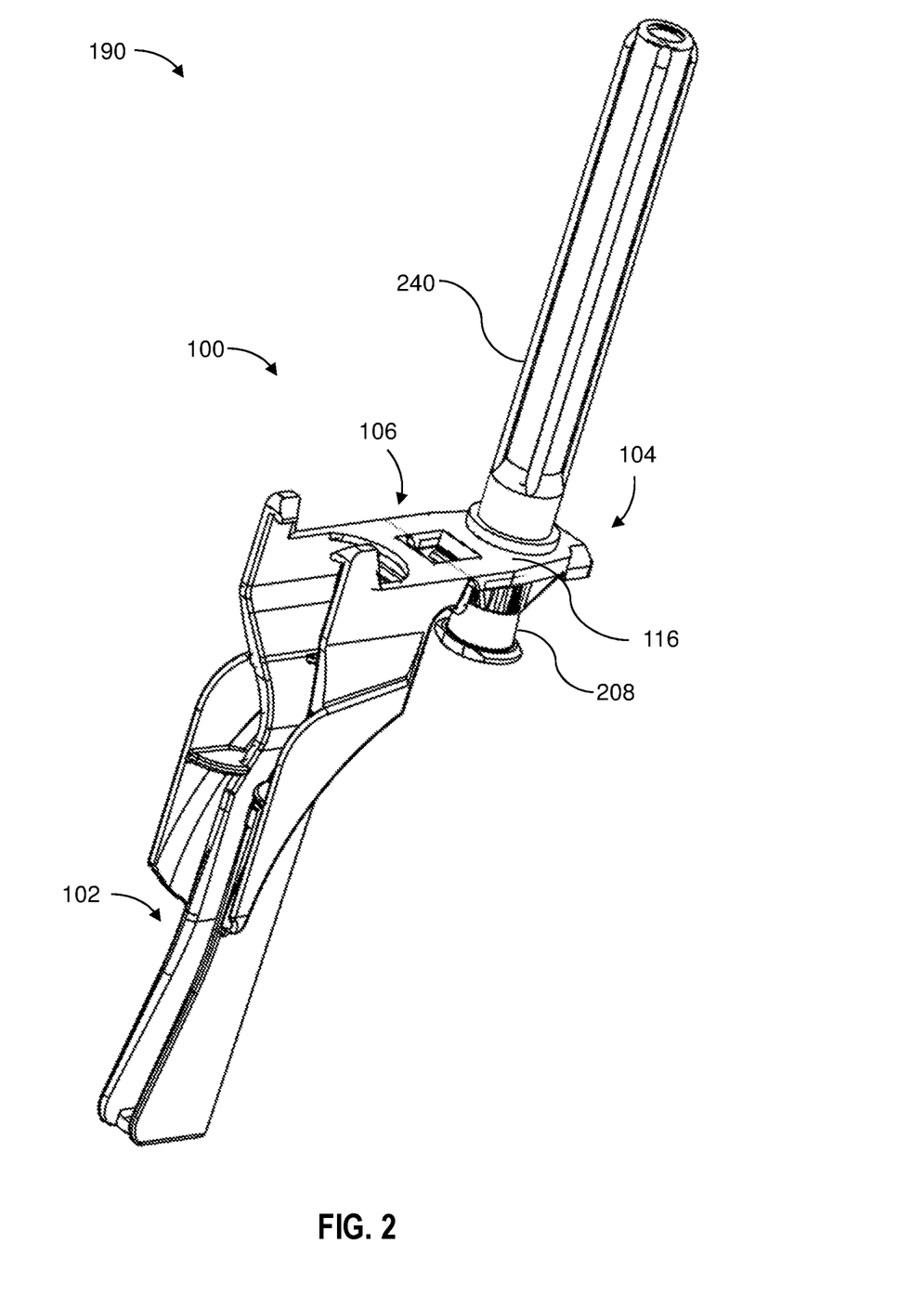
FIG. 2 is a top perspective view of the needle assembly shown in FIG. 1.
Figure 3:
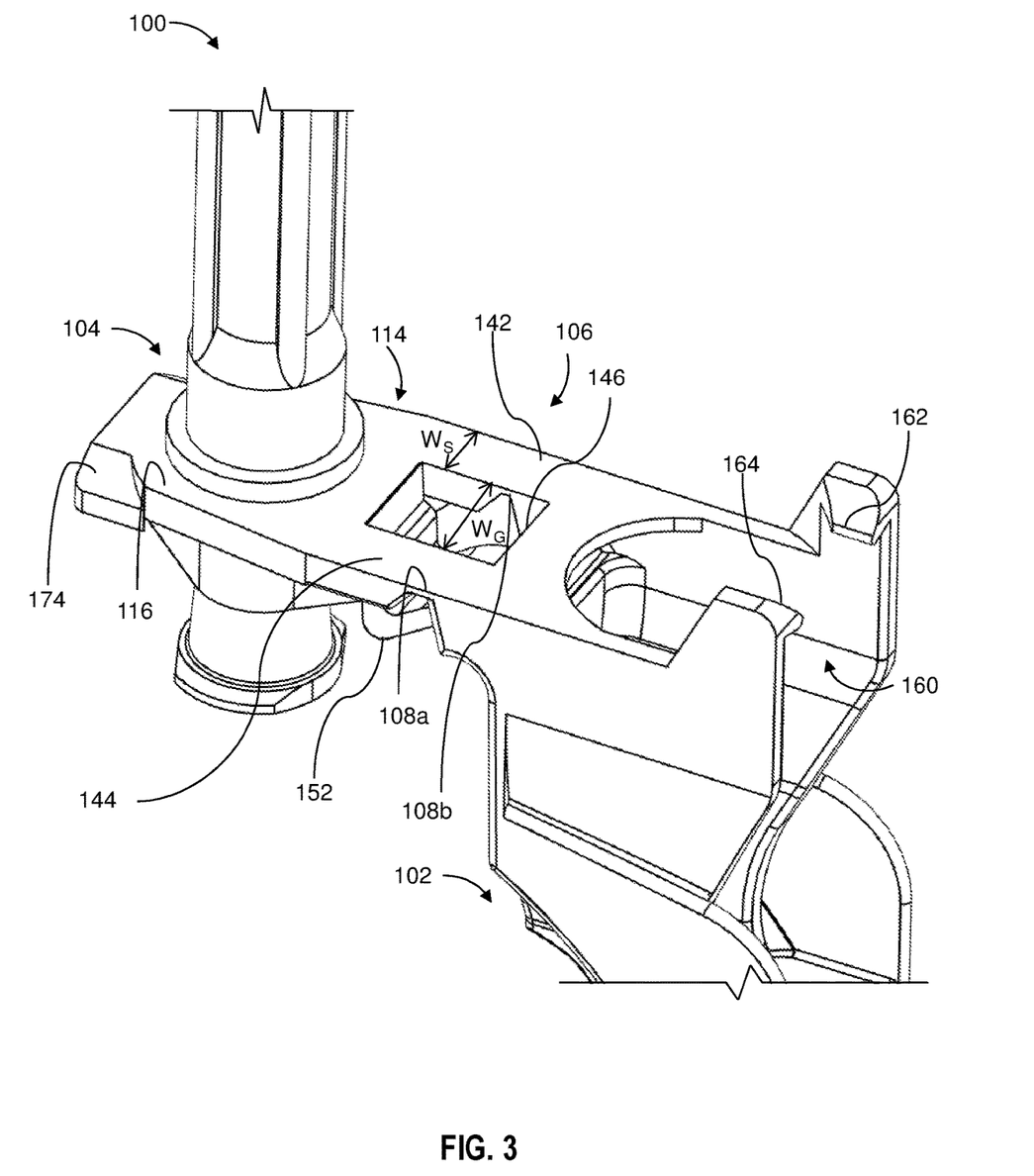
FIG. 3 a partial top perspective view of the needle assembly shown in FIG. 1.
Figure 4:
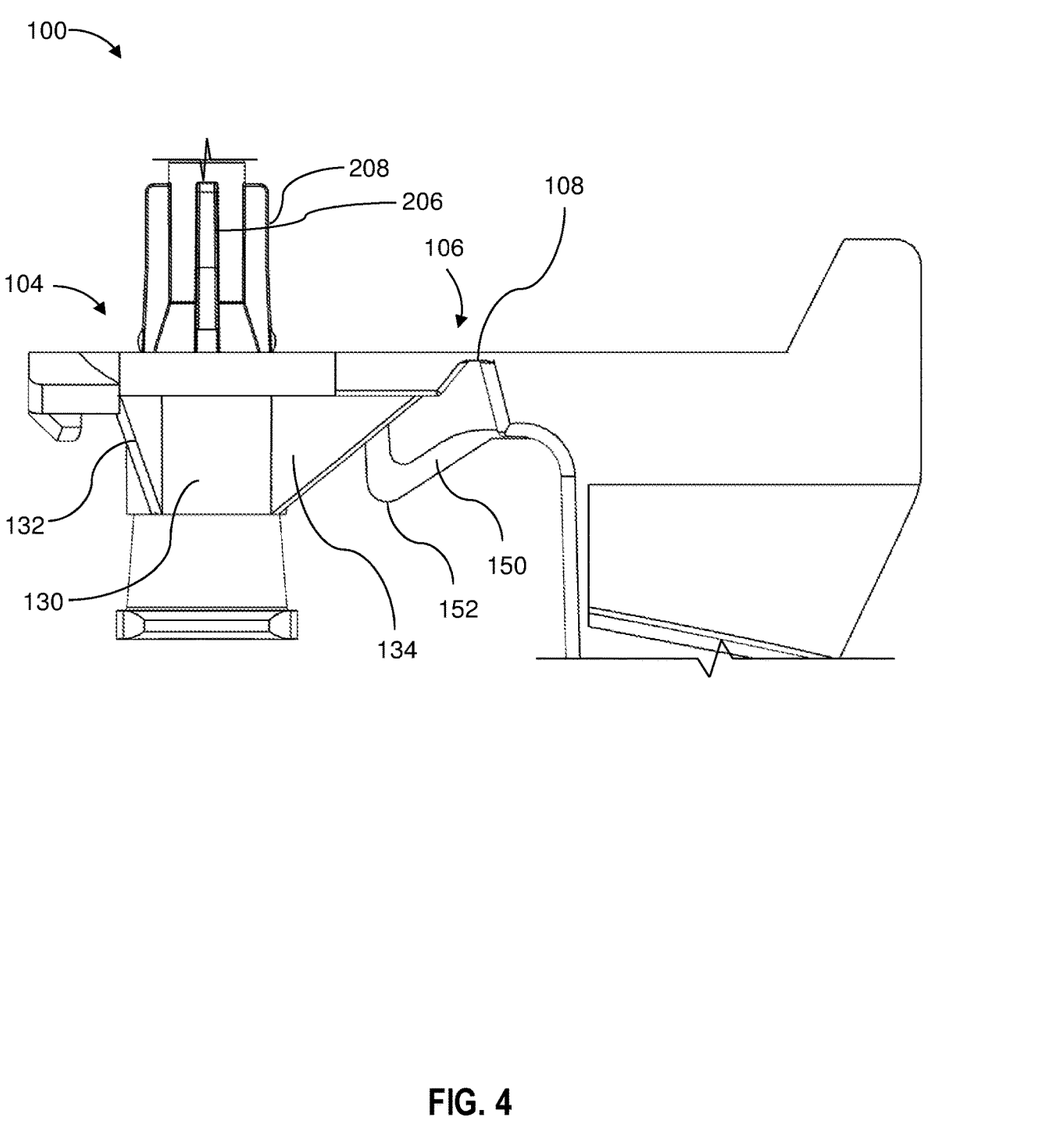
FIG. 4 is a partial side elevation view of the needle assembly shown in FIG. 1.
Figure 5:
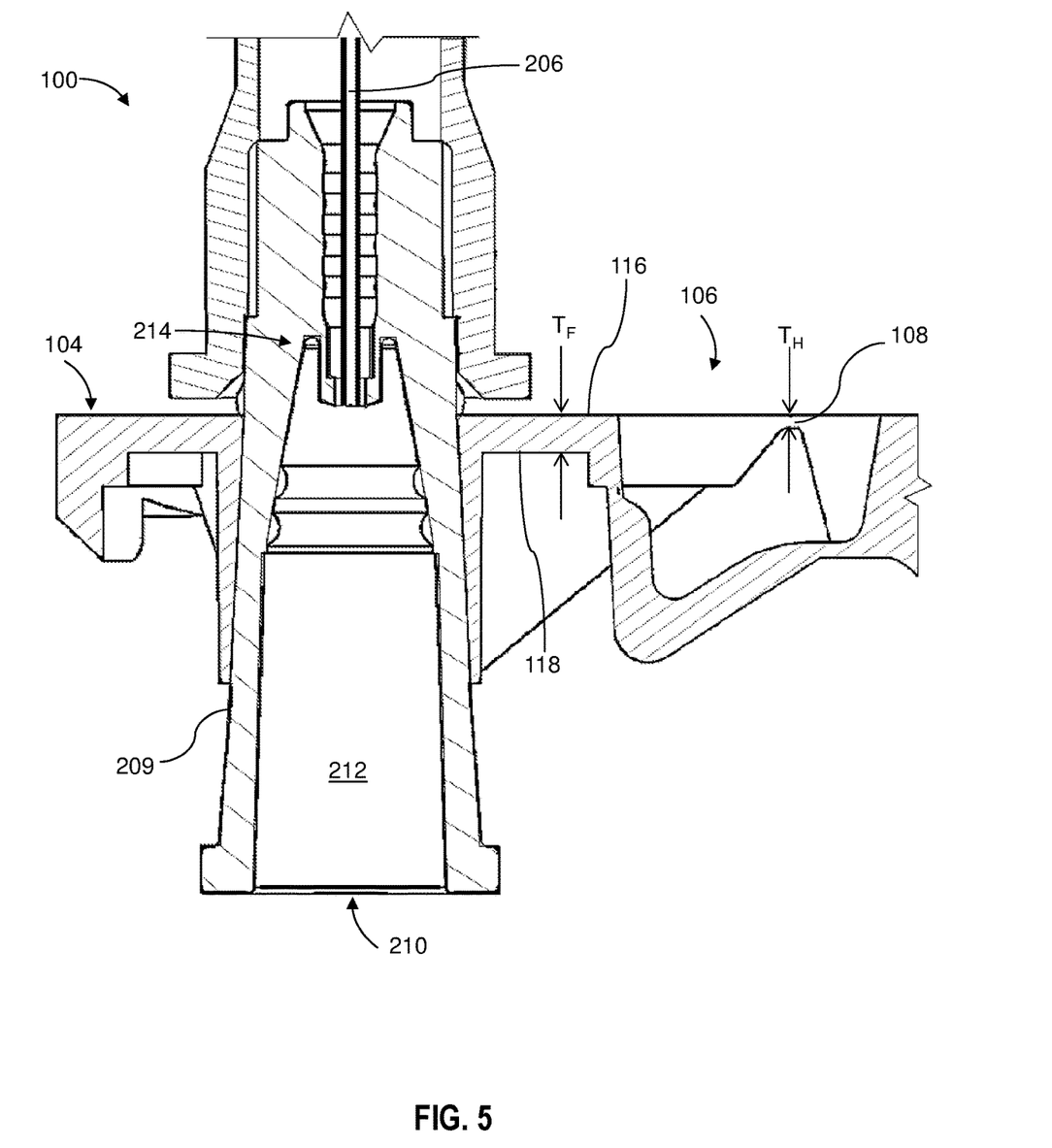
FIG. 5 is an enlarged cross-sectional side elevation view of the distal end of the syringe assembly of FIG. 1.

In one or more embodiments, the needle shield assembly 100 further comprises a leg 150 comprising a bend 152 connecting the shield portion 102 and the flange 114. As shown in FIG. 3 and FIG. 4, the leg 150 is disposed beneath the gap 146. The leg provides additional stability to the living hinge 108.

In some embodiments, the shield portion 102 further comprises a locking member 160 including two locking projections, a first locking projection 162 and a second locking projection 164, facing each other and projecting from the side walls 120, 122 and configured to engage with a locking tab 170. The locking tab 170 includes a first tab 172 and ramp 173 which cooperates with the first locking projection ramp 163 of the locking member 160 and a second tab 174 and ramp which cooperate with the second locking projection ramp 165 of the locking member 160. The first tab 172 and the second tab 174 of the locking tab 170 respectively push the first locking projection 162 and second locking projection 164 outwards. The first locking projection ramp 163 engages with the ramp 173 of the first tab 172 and the second locking projection ramp 165 engages with the ramp 173 of the second tab 174. After the first locking projection ramp 163 and the second locking projection ramp 165 are moved beyond the ramp 173 of the first tab 172 and the ramp 175 of the second tab 174, the locking projections 162, 164 snap locks to the locking tab 170 to secure the shield portion 102 in a protecting position 180. In this position, when the shield portion 102 is in the protected position 180 over the needle cover 240, the device is in the ready to use position. A medical practitioner can grip the shield portion 102 and rotate the shield portion 102 away from the needle cover 240, for example, as in the position shown in FIG. 1. When the practitioner is ready to inject a patient, the needle cover 240 is removed to expose the needle cannula 202. After injection of the patient, the shield portion is rotated so that the shield portion 102 is in a protected position 180 over the needle cannula 202.

In one or more embodiments, the shield portion 102, the bridge portion 106, the hub connection portion 104 and the living hinge 108 comprise a unitary structure integrally molded of thermoplastic material.

Another aspect of the disclosure pertains to a needle shield and needle assembly comprising the needle assembly 100 shown and described herein including the needle cannula 202 having a proximal end 203, a distal end 205 and a lumen 206 therethrough, and a hub 208 having an outer surface 209, an open proximal end 210 including a cavity 212 therein and a distal end 214 attached to the proximal end of the needle cannula 202 so that the lumen 206 is in fluid communication with the cavity 212. The needle shield and needle assembly comprise the elongate needle shield 100 comprising a shield portion 102, a hub connection portion 104 and a bridge portion 106 including a living hinge 108 having a thickness TH, the bridge portion 106 joining the hub connection 104 portion and the shield portion 102. The hub connection portion comprises a receiving ring 112 having a diameter D sized to frictionally receive the hub outer surface 209 when the needle assembly 200 is inserted through the receiving ring 112 and a flange 114 extending from the receiving ring 112 defining a top planar surface 116 and a bottom surface 118. The flange 114 has a thickness TF, the thickness of the flange TF divided by the thickness of the living hinge TH defining a ratio of from 1.1 to 6.

In one or more embodiments, the thickness of the flange TF divided by the thickness of the living hinge TH defines a ratio of from 1.2 to 6, 1.3 to 6, 1.4 to 6, 1.5 to 6, 1.6 to 6, 1.7 to 6, 1.8 to 6, 1.9 to 6, 2 to 6, 2.1 to 6, 2.2 to 6, 2.3 to 6, 2.4 to 6, 2.5 to 6, 2.6 to 6, 2.7 to 6, 2.8 to 6, 2.9 to 6, 3 to 6, 1.1 to 5, 1.2 to 5, 1.3 to 5, 1.4 to 5, 1.5 to 5, 1.6 to 5, 1.7 to 5, 1.8 to 5, 1.9 to 5, 2 to 5, 2.1 to 5, 2.2 to 5, 2.3 to 5, 2.4 to 5, 2.5 to 5, 2.6 to 5, 2.7 to 5, 2.8 to 5, 2.9 to 5, 3 to 5, 1.1 to 4, 1.2 to 4, 1.3 to 4, 1.4 to 4, 1.5 to 4, 1.6 to 4, 1.7 to 4, 1.8 to 4, 1.9 to 4, 2 to 4, 2.1 to 4, 2.2 to 4, 2.3 to 4, 2.4 to 4, 2.5 to 4, 2.6 to 4, 2.7 to 4, 2.8 to 4, 2.9 to 4, 3 to 4.

If the thickness of the living hinge TH is too great, the living hinge will not be flexible enough, and the shield will not be easily closed over the needle cannula. On the other hand, if the thickness of the living hinge TH is too small, the living hinge will be prone to breaking. In one or more embodiments, the ratio defined by the thickness of the flange TF divided by the thickness of the living hinge TH is within the above provided ranges. If the ratio defined by the thickness of the flange TF divided by the thickness of the living hinge TH is outside the defined ranges, the needle shield will be difficult to manufacture by injection molding because when the ratio is too low, insufficient material will flow to form the bridge portion 106 and the hub connection portion 104 of the needle shield assembly 100. In one or more embodiments, in addition to being within the ratios provided above, the living hinge 108 has a thickness TH in a range of from 0.1 mm to 0.3 mm, for example 0.1 mm, 0.15 mm, 0.2 mm, 0.25 mm or 0.3 mm) and the flange TF 114 has a thickness in a range of from 0.4 mm to 0.8 mm (for example 0.4 mm, 0.45 mm, 0.5 mm, 0.55 mm, 0.60 mm, 0.65 mm, 0.70 mm, 0.75 mm or 0.80 mm).

The shield portion 102 has two side walls, a first side wall 120 and a second sidewall 122, defining a longitudinal opening 124 and a back wall 126 between the side walls 120,122 defining a recess 127 having an interior surface 128. The shield portion 102 is configured to pivot from an open position in which the needle cannula is exposed (see e.g., FIG. 1 and FIG. 7), to a closed protected position 180 in which the distal end 205 of the needle cannula 202 is protected within the longitudinal opening 124 of the shield.

Figure 6A:
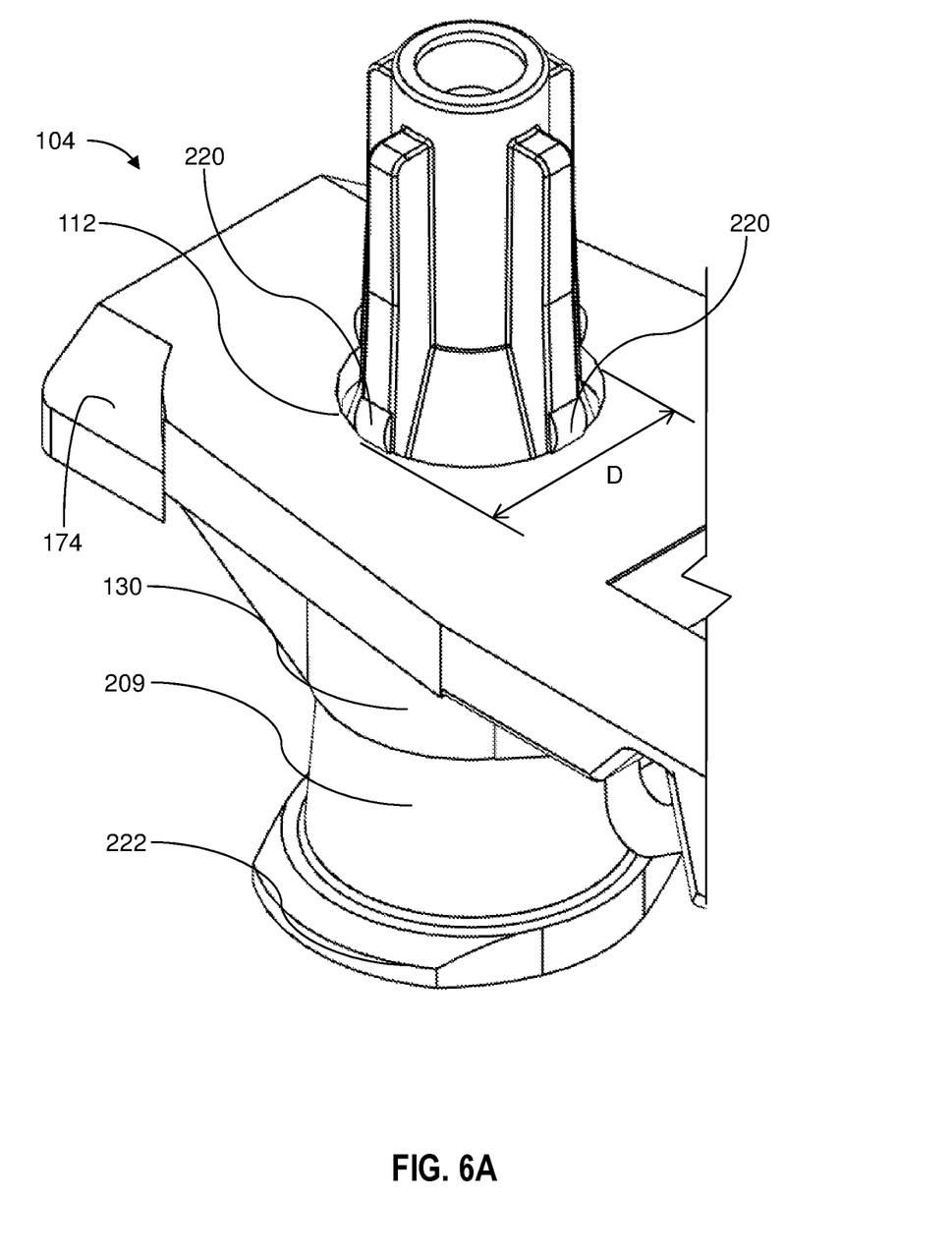
FIG. 6A is a top partial perspective view of a portion of the needle assembly shown in FIG. 1.

In one or more embodiments, the needle shield and needle assembly further comprises a plurality of radial projections 220 extending from the needle hub, the radial projections 220 spaced from the open proximal end 210 so that the hub 208 remains seated in the receiving ring 112 when the needle assembly 200 has been inserted through the receiving ring. As best shown in FIG. 6A, the radial projections 220 are engaged with the periphery of the receiving ring 112 to prevent the hub 208 from being moved through the flange. The radial projections 220 are configured to prevent the hub 208 from being moved in a proximal direction to be pushed through the receiving ring 112.

In an exemplary use of the disclosure, a practitioner unpacks needle shield assembly 100 from packaging in an open position 190. The practitioner assembles and secures syringe 310 to hub 208 of needle assembly 200. Once syringe 310 has been engaged with the hub 208, the needle cover 240 is removed from the needle assembly 200 and injection occurs. The practitioner removes the needle cannula 202 from the patient. Either with or without the syringe 310 secured to the hub 208 of the needle assembly 200, practitioner rotates the hub connection portion 104 about the bridge portion 106 to toggle the needle shield assembly 100 from the open position 190 to the protected position 180. In the protected position 180, the locking tab 170 and the locking member 160 are fully engaged, thus shielding the needle cannula 202 from accidental post-injection needle sticks.

Figure 6B:
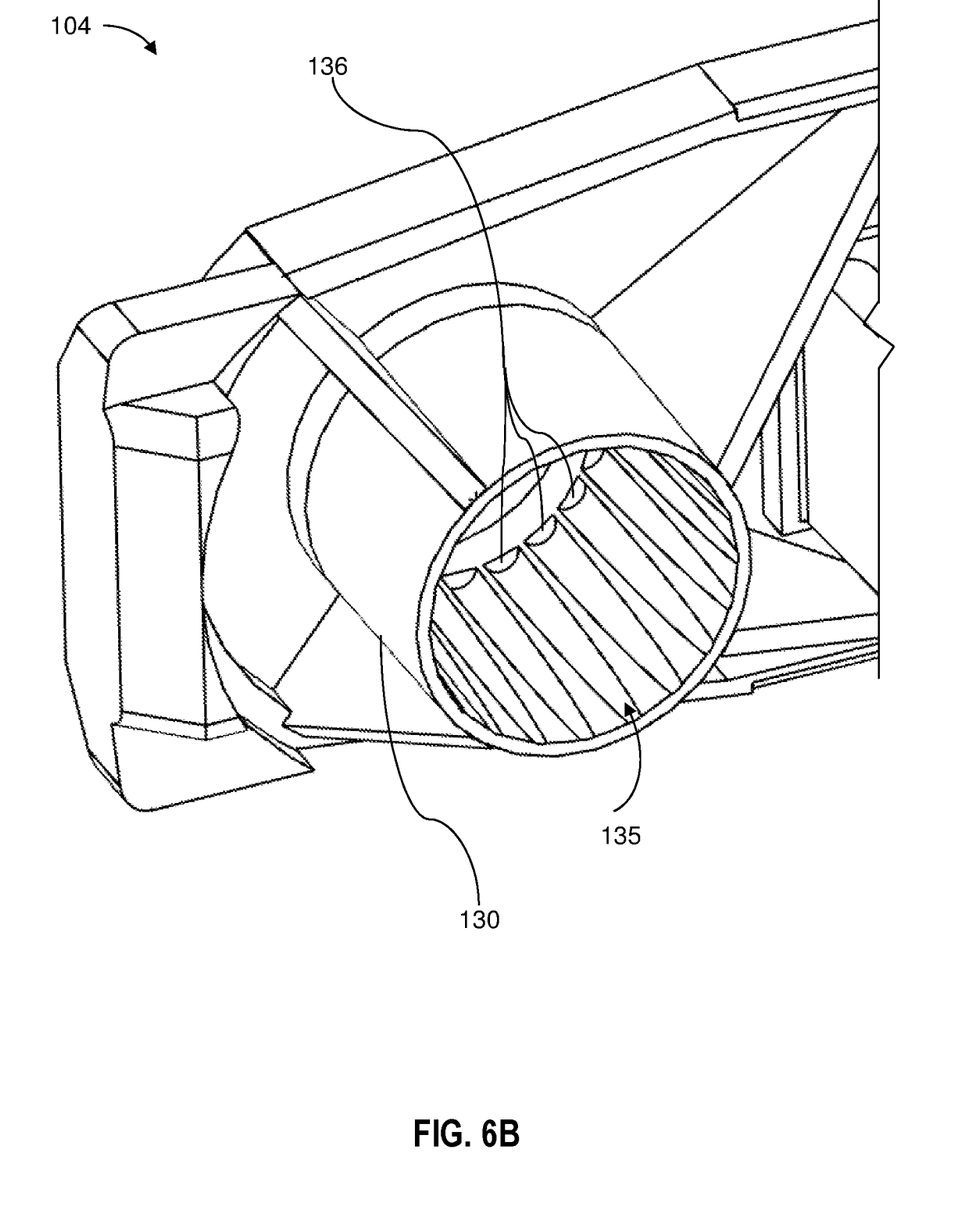
FIG. 6B is a bottom partial enlarged perspective view of the receiving ring of the needle assembly shown in FIG. 1.
Figure 6C:
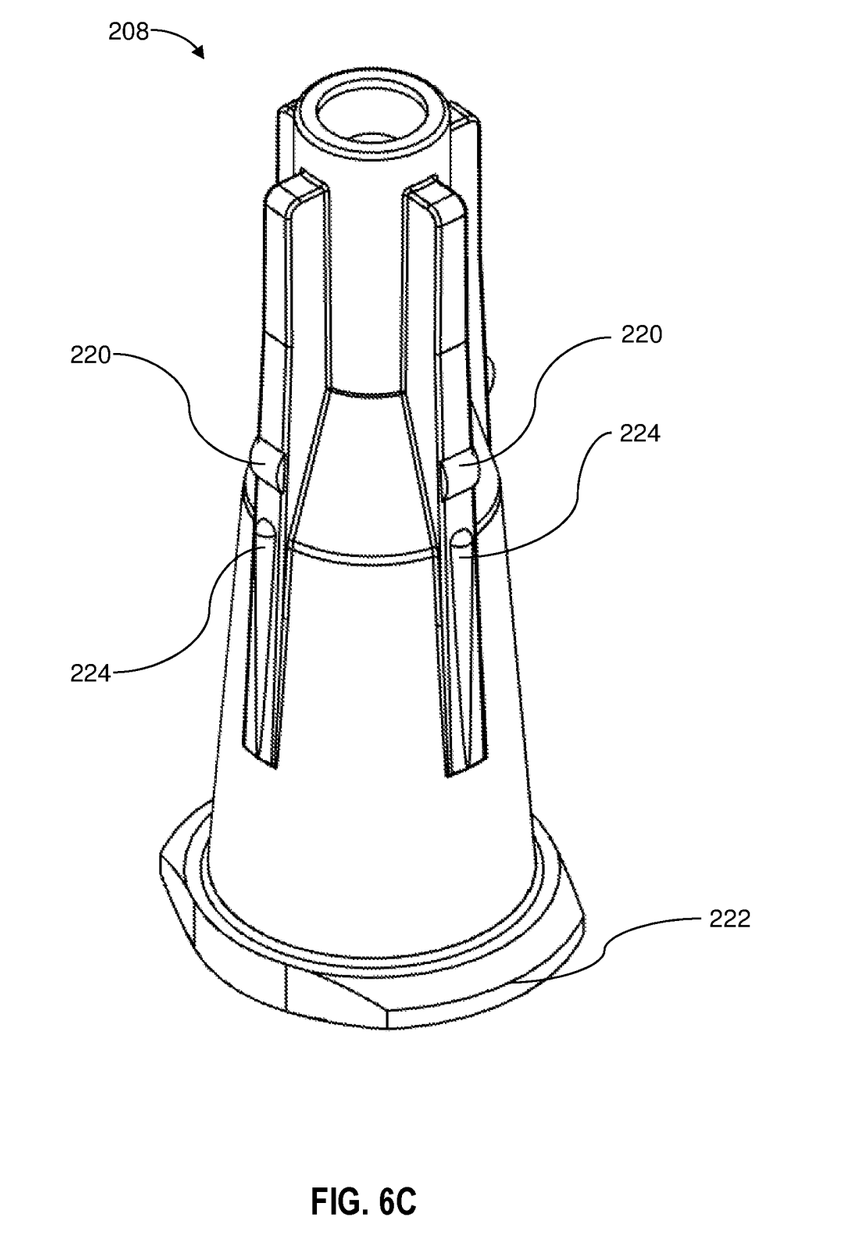
FIG. 6C is an enlarged perspective view of the hub of the needle assembly.
Figure 7:
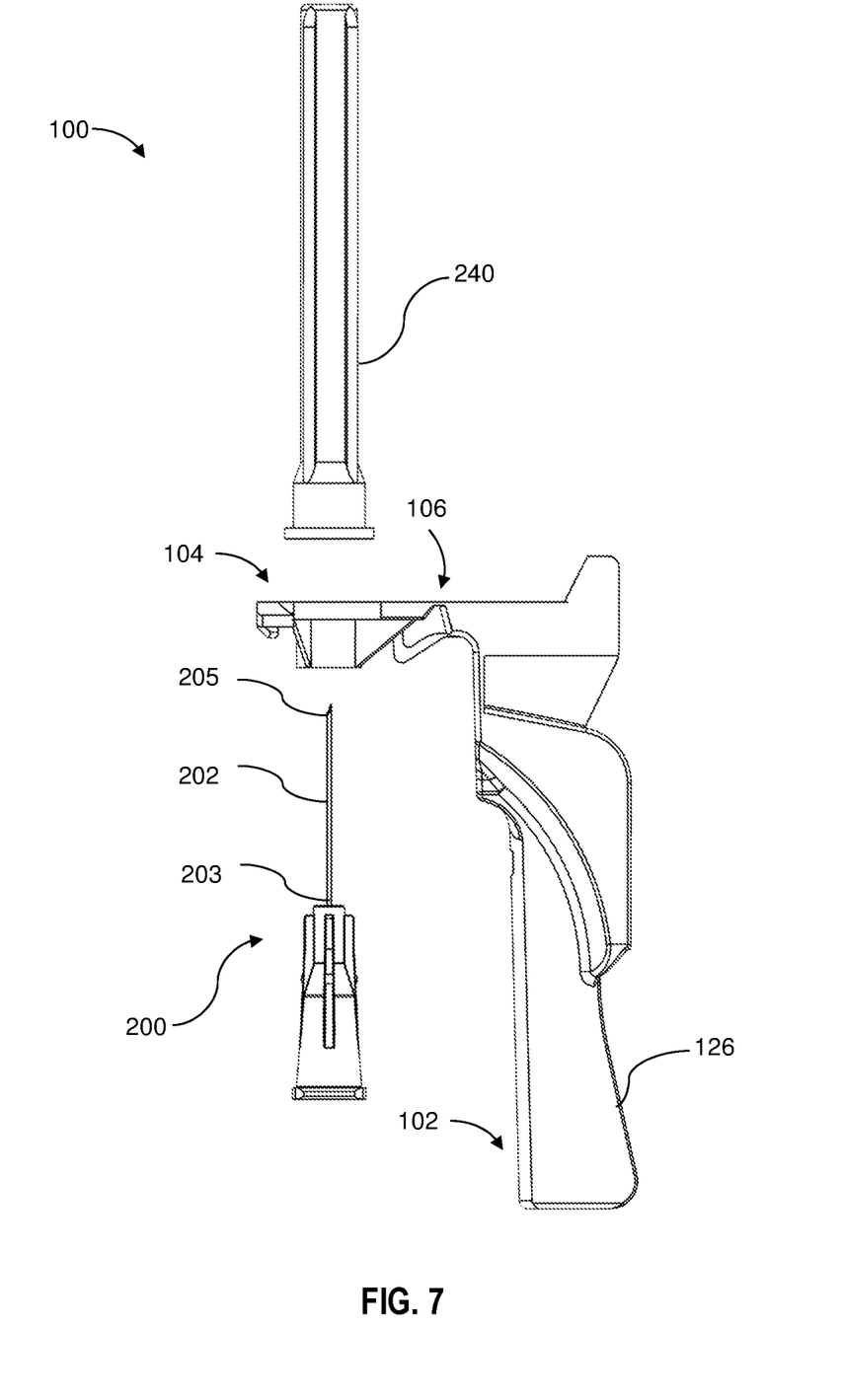
FIG. 7 is an exploded side elevation view of a needle assembly of the needle assembly shown in FIG. 1.

Referring now to FIG. 6B, the cylindrical wall extension which extends below the bottom surface 118 of the flange 114 and provides a cylindrical receiving structure 130 for the hub 208 comprises an inner surface 135 and splines 136. FIG. 6C shows the hub as having complementary hub splines 224 which are configured to engage the spline 136 on the inner surface 135 of the cylindrical receiving structure 130. In the embodiment shown, the splines 136 are hollow sections on the inner surface 135, and the hub splines 224 are elongate radial protrusions that are complementary to and configured to seat within the splines 136. Thus, the splines 136 are female splines and the hub splines 224 are male splines. It will be understood that this figuration could be reversed. In the embodiment shown, twenty-four splines 136 are shown on the inner surface 135 of the cylindrical receiving structure 130. In this configuration, the splines are space apart by 15 degrees around the periphery of the cylindrical receiving structure 130. It will be understood that the number of splines can be varied so that the splines are spaced apart by 10 degrees (36 splines), 15 degrees (24 splines) 20 degrees (18 splines), 30 degrees (12 splines), 40 degrees (9 splines), 45 degrees (8 splines) 60 degrees (6 splines), 72 degrees (5 splines) or 90 degrees (4 splines). There are four hub splines 224 shown in FIG. 6C, and this number can vary and include one, two, three, four, five, six, seven, eight, nine or then hub splines 224.

The hub splines 224 and the splines 136 are configured to cooperate to allow rotation of the hub 208 with respect to the shield portion 102. The hub splines 224 and the splines 136 in some embodiments are configured to create a tactile or perceptible click during each rotation as the hub splines 224 and the splines 136 engage and disengage each other as the hub 208 is rotated with respect to the shield portion.

In one or more embodiments, toggling the needle shield assembly 100 from open position 190 to protected position 180 may be completed in a variety of ways. During injection, the practitioner may be required to use one hand to press the injection site with a sanity cloth or pad during or after injection. The practitioner can remove the needle cannula 202 from the skin and single-handedly toggle the needle shield assembly 100 by rotating the syringe, thus using the weight of the shield portion 102 to fold over the hub connection portion 104 and fully engage the protected position 180. Additionally, a practitioner may use a flat surface like a patient table, for example, to rotate the shield portion 102 about the bridge portion 106 to engage the protected position 180.

In one or more embodiments, a needle cannula clip (not shown) may be disposed within the longitudinal opening 124 of the shield portion 102 configured to receive the needle cannula 202 to increase shielding while the needle shield assembly 100 is in the protected position 180.

In one or more embodiments, after an injection is performed, a practitioner can remove the needle assembly 200 from the receiving ring 112 of the hub connection portion 104 while the needle shield assembly 100 is engaged in the protected position 180.

In one or more embodiments, the hub 208 is rotatable within the receiving ring 112. The outside diameter of the hub 208 at the complementary hub splines 224 is configured so that there is a friction fit between the hub 208 and the receiving ring 112, allowing rotation of the hub 208 to be set by the practitioner, but not too loose to allow free rotation. This configuration permits a proper or a preferred orientation of a bevel on the needle cannula 202 to be varied depending on a particular medical procedure. For example, subcutaneous, intravenous or intradermal types of injections typically require the needle to be inserted at various angles in relation to the patient's skin (e.g., 45 degrees, 25 degrees, 10 degrees respectively), with the needle bevel typically in the up position (facing away from the skin surface) and the bevel visible to the clinician. As such, it is advantageous for the hub 208 to be rotated to a position such that the needle bevel is not obstructing the clinician's view of the needle bevel. In intermuscular injection, the bevel is typically 90 degrees to the patient's skin. As such, the needle bevel rotational orientation in relation to the safety needle cover does not matter because the clinician does not need to see the bevel orientation.

Figure 9:
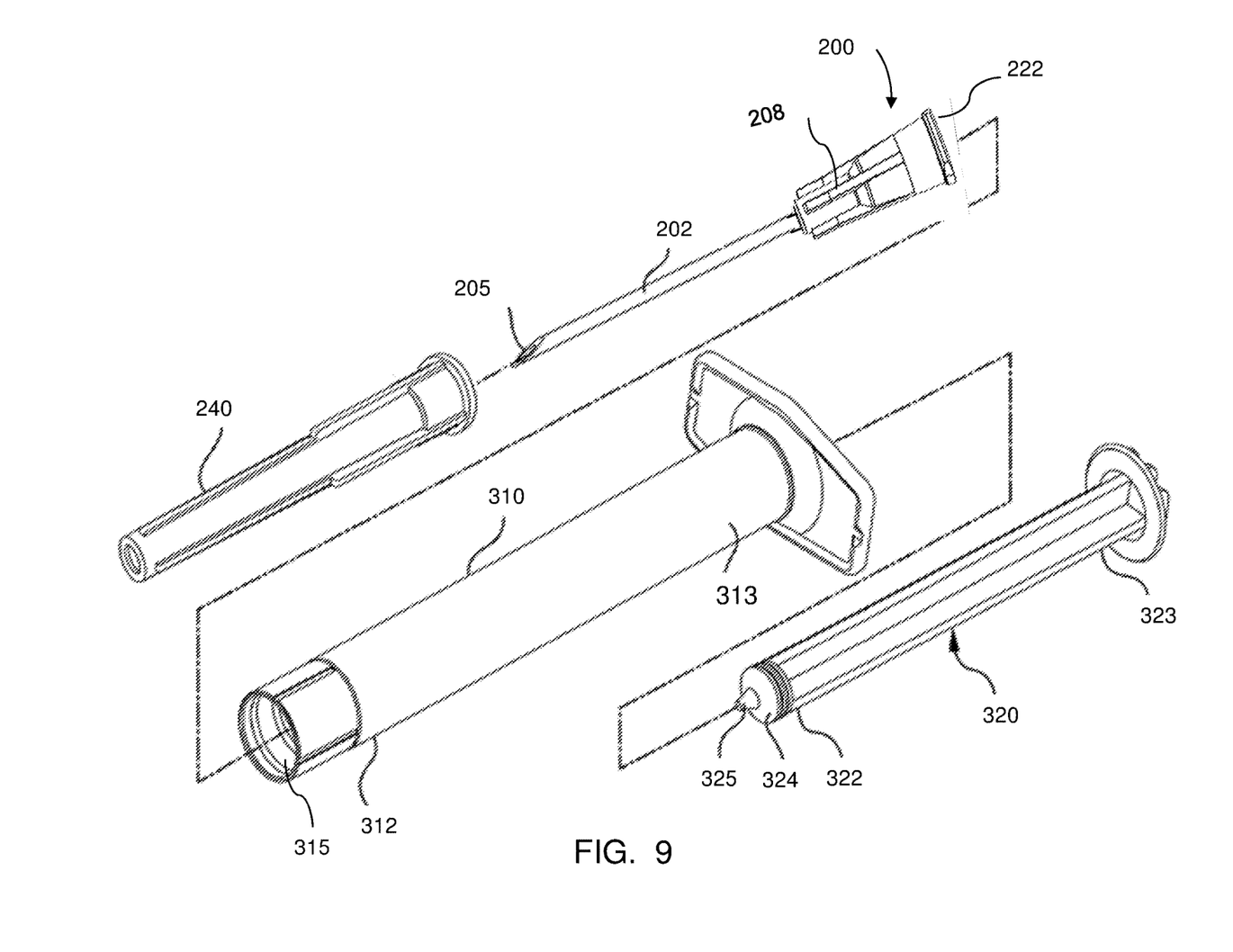
FIG. 9 is an exploded perspective view of a syringe and needle assembly.

In one or more embodiments, the open proximal end 210 of the hub 208 comprises lugs 222 that are configured to be engaged with a threaded collar 315 of a syringe 310 having a distal end 312 and a proximal end 313 so that the needle shield and needle assembly connectable to the syringe 310. As shown in FIG. 9, the syringe 310 may further comprise a plunger 320 having a distal end 322 and a proximal end 323. The distal end 322 may include a stopper 324 having a distal tip 325. In use the hub 208 shown in FIG. 9 can be inserted in the receiving ring 112 of the needle shield assembly 100, and the syringe 310 can be connected to the hub by engaging the lugs 222 with threaded collar 314 of the syringe 310.

The plunger 320 can be positioned in fluid-tight engagement with the inside surface of the barrel of the syringe for drawing fluid into and driving fluid out of the barrel chamber by movement of the stopper relative to the barrel. The elongate body portion extends outwardly from the open end of the barrel.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A needle shield assembly for use with a needle assembly including a needle cannula having a proximal end, a distal end and a lumen therethrough, and a hub having an outer surface further comprising a plurality of radial projections and a plurality of hub splines extending radially from the hub, an open proximal end spaced from the radial projections and the hub splines including a cavity therein and a distal end attached to the proximal end of the needle cannula so that the lumen is in fluid communication with the cavity, the needle shield assembly comprising:
an elongate needle shield comprising a shield portion, a hub connection portion and a bridge portion including a living hinge having a thickness, the bridge portion joining the hub connection portion and the shield portion, the hub connection portion comprising a receiving ring having a diameter sized to frictionally receive the hub outer surface when the needle assembly is inserted through the receiving ring and a flange extending from the receiving ring defining a top planar surface and a bottom surface, the hub being rotatable within the receiving ring, a cylindrical wall extension having an inner surface with splines that are configured to cooperate with hub splines on a needle hub when a needle hub is engaged with the cylindrical wall extension, wherein the hub splines and the splines are configured to create a tactile or perceptible click during each rotation as the hub splines and the splines engage and disengage each other as the hub is rotated with respect to the shield portion, the shield portion having two side walls defining a longitudinal opening and a back wall between the side walls defining a recess having an interior surface, the shield portion configured to pivot from an open position in which the needle cannula is exposed, to a closed needle protecting position in which the distal end of the needle cannula is within the longitudinal opening of the shield.

2. The needle shield assembly of claim 1, the receiving ring further comprising the cylindrical wall extension which extends below the bottom surface of the flange to provide a cylindrical receiving structure.

3. The needle shield assembly of claim 2, further comprising a plurality of ribs extending from the bottom surface and radially extending from the cylindrical wall extension.

4. The needle shield assembly of claim 3, wherein the plurality of ribs comprises from 3 to 8 ribs.

5. The needle shield assembly of claim 4, wherein the plurality of ribs comprises from 3 to 5 ribs.

6. The needle shield assembly of claim 1, the bridge portion comprising a first span spaced apart from a second span to provide a gap between the first span and the second span, and the living hinge having a first portion joining the first span to the shield portion and a second portion joining the second span to the shield portion.

7. The needle shield assembly of claim 6, the first span and the second span each comprise a width and the gap comprises a width such that the width of the gap is greater than the width of the first span and the width of the second span.

8. The needle shield assembly of claim 7, further comprising a leg comprising a bend connecting the shield portion and the flange.

9. The needle shield assembly of claim 1, the living hinge having a thickness in a range of from 0.1 mm to 0.3 mm and the flange having a thickness in a range of from 0.4 mm to 0.8 mm.

10. The needle shield assembly of claim 1, the shield portion further comprising a locking member including two locking projections facing each other and projecting from the side walls and configured to engage with a needle cover placed over the needle cannula when the shield in the closed position to a locking tab extending from the flange.

11. The needle shield assembly of claim 1, the shield portion, the bridge portion, the hub connection portion and the living hinge comprising a unitary structure integrally molded of thermoplastic material.

12. A needle shield and needle assembly comprising:
a needle assembly including a needle cannula having a proximal end, a distal end and a lumen therethrough, and a hub having an outer surface further comprising a plurality of radial projections and a plurality of hub splines extending radially from the hub, an open proximal end spaced from the radial projections and the hub splines including a cavity therein and a distal end attached to the proximal end of the needle cannula so that the lumen is in fluid communication with the cavity; and
an elongate needle shield comprising a shield portion, a hub connection portion and a bridge portion including a living hinge having a thickness, the bridge portion joining the hub connection portion and the shield portion, the hub connection portion comprising a receiving ring having a diameter sized to frictionally receive the hub outer surface when the needle assembly is inserted through the receiving ring and a flange extending from the receiving ring defining a top planar surface and a bottom surface, the hub being rotatable within the receiving ring, the cylindrical wall extension having an inner surface with splines that are configured to cooperate with hub splines on a needle hub when a needle hub is engaged with the cylindrical wall extension, wherein the hub splines and the splines are configured to create a tactile or perceptible click during each rotation as the hub splines and the splines engage and disengage each other as the hub is rotated with respect to the shield portion, the flange having a thickness, the thickness of the flange divided by the thickness of the living hinge defining a ratio of from 1.1 to 6, the shield portion having two side walls defining a longitudinal opening and a back wall between the side walls defining a recess having an interior surface, the shield portion configured to pivot from an open position in which the needle cannula is exposed, to a closed needle-protecting position in which the distal end of the needle cannula is within the longitudinal opening of the shield.

13. The needle shield and needle assembly of claim 12, the receiving ring further comprising a cylindrical wall extension which extends below the bottom surface of the flange to provide a cylindrical receiving structure.

14. The needle shield and needle assembly of claim 13, further comprising a plurality of ribs extending from the bottom surface and radially extending from the cylindrical wall extension.

15. The needle shield and needle assembly of claim 14, wherein the plurality of ribs comprises from 3 to 8 ribs.

16. The needle shield and needle assembly of claim 14, wherein the plurality of ribs comprises from 3 to 5 ribs.

17. The needle shield and needle assembly of claim 12, the bridge portion comprising a first span spaced apart from a second span to provide a gap between the first span and the second span, and the living hinge having a first portion joining the first span to the shield portion and a second portion joining the second span to the shield portion.

18. The needle shield and needle assembly of claim 17, the first span and the second span each comprise a width and the gap comprises a width such that the width of the gap is greater than the width of the first span and the width of the second span.

19. The needle shield and needle assembly of claim 18, further comprising a leg comprising a bend connecting the shield portion and the flange.

20. The needle shield and needle assembly of claim 12, the living hinge having a thickness in a range of from 0.1 mm to 0.3 mm and the flange having a thickness in a range of from 0.4 mm to 0.8 mm.

21. The needle shield and needle assembly of claim 12, the shield portion further comprising a locking member including two locking projections facing each other and projecting from the side walls and configured to engage with a needle cover placed over the needle cannula when the shield is in the closed position to a locking tab extending from the flange.

22. The needle shield and needle assembly of claim 12, the shield portion, the bridge portion, the hub connection portion and the living hinge comprising a unitary structure integrally molded of thermoplastic material.

23. The needle shield and needle assembly of claim 12, the radial projections spaced from proximal end so that the hub remains seated in the receiving ring.

24. The needle shield and needle assembly of claim 12, the proximal end of the hub comprising lugs that are configured to be engaged with a threaded collar of a syringe so that the needle shield and needle assembly connectable to the syringe.

25. The needle shield and needle assembly of claim 12, wherein the splines are hollow sections on the inner surface, and the hub splines are elongate radial protrusions that are complementary to and configured to seat within the splines.

26. The needle shield and needle assembly of claim 25, wherein the hub splines and the splines are configured to cooperate to allow rotation of the hub with respect to the shield portion.

* * * * *